US012478753B2

(12) United States Patent
Rose et al.

(10) Patent No.: US 12,478,753 B2
(45) Date of Patent: Nov. 25, 2025

(54) VENT FOR A COMPONENT OF A RESPIRATORY THERAPY SYSTEM

(71) Applicant: Fisher & Paykel Healthcare Limited, Auckland (NZ)

(72) Inventors: Hamish Joshua Rose, Auckland (NZ); Max Leon Betteridge, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 677 days.

(21) Appl. No.: 16/312,503

(22) PCT Filed: Jul. 7, 2017

(86) PCT No.: PCT/NZ2017/050093
§ 371 (c)(1),
(2) Date: Dec. 21, 2018

(87) PCT Pub. No.: WO2018/009080
PCT Pub. Date: Jan. 11, 2018

(65) Prior Publication Data

US 2019/0160249 A1 May 30, 2019

Related U.S. Application Data

(60) Provisional application No. 62/359,919, filed on Jul. 8, 2016.

(51) Int. Cl.
*A61M 16/06* (2006.01)
*A61M 16/08* (2006.01)

(52) U.S. Cl.
CPC ........ *A61M 16/0683* (2013.01); *A61M 16/06* (2013.01); *A61M 16/0633* (2014.02);
(Continued)

(58) Field of Classification Search
CPC .............. A61M 16/0683; A61M 16/06; A61M 2202/0225; A61M 2205/42; A61M 16/0825; A61M 16/0633
See application file for complete search history.

(56) References Cited

U.S. PATENT DOCUMENTS 6,581,594 B1 * 6/2003 Drew .................... A61M 16/06 128/204.18
6,851,425 B2 * 2/2005 Jaffre .................... A61M 16/08 128/204.18
(Continued)

FOREIGN PATENT DOCUMENTS

WO WO 2001/095965 A1 12/2001
WO WO 2005/018523 A2 3/2005
(Continued)

OTHER PUBLICATIONS

International Search Report, PCT/NZ2017/050093, dated Sep. 11, 2017, 7 pages.

*Primary Examiner* — Justine R Yu
*Assistant Examiner* — Gwynneth L Howell
(74) *Attorney, Agent, or Firm* — VIA LLP

(57) ABSTRACT

A vent for venting exhaust gases from a component of a respiratory therapy system. The vent may include a substrate having an inner surface and an outer surface. The vent may include at least one vent hole 17 extending through the substrate and having a vent hole circumference. The vent hole may include an exhaust gas inlet at the inner margin of the substrate and an exhaust gas outlet at an outer margin of the substrate. The vent hole may include a sidewall extending between the exhaust gas inlet and the exhaust gas outlet. The exhaust gas inlet and the exhaust gas outlet have different diameters such that the sidewall of the vent hole is inclined at an angle of inclination between the exhaust gas inlet and the exhaust gas outlet. The angle of inclination of
(Continued)

the inclined side wall of the vent is non-constant around the vent hole circumference.

15 Claims, 11 Drawing Sheets

(52) U.S. Cl.
CPC . *A61M 16/0825* (2014.02); *A61M 2202/0225* (2013.01); *A61M 2205/42* (2013.01)

(56) References Cited

U.S. PATENT DOCUMENTS

| | | | | |
|---|---|---|---|---|
| 6,907,882 | B2 * | 6/2005 | Ging | A62B 18/084 128/207.11 |
| 8,205,615 | B1 * | 6/2012 | Ho | A61M 16/06 128/205.24 |
| 8,573,201 | B2 * | 11/2013 | Rummery | A62B 9/04 128/202.27 |
| 8,851,074 | B2 * | 10/2014 | Chien | A61M 16/0666 128/206.27 |
| D743,022 | S * | 11/2015 | Chien | D24/110.4 |
| D743,537 | S * | 11/2015 | Answine | D24/110.5 |
| 11,027,085 | B2 * | 6/2021 | Grashow | A61M 16/06 |
| 2005/0241644 | A1 | 11/2005 | Gunaratnam et al. | |
| 2007/0044804 | A1 * | 3/2007 | Matula | A61M 16/0638 128/206.21 |
| 2008/0168991 | A1 | 7/2008 | Eifler | |
| 2009/0050156 | A1 * | 2/2009 | Ng | A61M 16/06 128/205.24 |
| 2011/0155140 | A1 * | 6/2011 | Ho | A61M 16/0666 128/207.18 |
| 2011/0240030 | A1 * | 10/2011 | Ho | A61M 16/06 128/206.21 |
| 2012/0138061 | A1 * | 6/2012 | Dravitzki | A61M 16/0633 128/205.25 |
| 2013/0239972 | A1 * | 9/2013 | McAuley | A61M 16/0616 128/205.25 |
| 2014/0150798 | A1 | 6/2014 | Fong | |
| 2014/0311496 | A1 * | 10/2014 | Rothermel | A61M 16/0622 128/206.24 |
| 2015/0265795 | A1 * | 9/2015 | Voncken | A61M 16/0655 128/206.24 |
| 2015/0283348 | A1 * | 10/2015 | Harp | A61M 16/0683 128/205.25 |
| 2016/0008566 | A1 * | 1/2016 | Partington | A61M 16/0622 128/201.13 |
| 2016/0022944 | A1 * | 1/2016 | Chodkowski | A61M 16/0616 128/206.24 |
| 2016/0051784 | A1 * | 2/2016 | Eury | A61M 16/0666 128/207.18 |
| 2016/0074611 | A1 * | 3/2016 | Higgins | A61M 16/0605 128/206.24 |
| 2016/0074683 | A1 * | 3/2016 | Bergeron | A62B 18/006 128/201.19 |
| 2016/0082216 | A1 * | 3/2016 | Lynch | A61M 16/0683 128/205.25 |
| 2016/0184549 | A1 * | 6/2016 | Bugamelli | A61M 16/06 128/205.24 |
| 2016/0279359 | A1 * | 9/2016 | Chang | A61M 16/0051 |
| 2016/0296720 | A1 * | 10/2016 | Henry | A61M 16/0622 |
| 2016/0310688 | A1 * | 10/2016 | Rothermel | A61M 16/0816 |
| 2016/0325067 | A1 * | 11/2016 | Harwood | A61M 16/0875 |
| 2016/0375214 | A1 * | 12/2016 | Chodkowski | B32B 5/245 128/206.21 |
| 2017/0080263 | A1 * | 3/2017 | Chiu | A61M 16/06 |
| 2017/0157435 | A1 * | 6/2017 | Choi | A41D 13/1107 |
| 2017/0246414 | A1 * | 8/2017 | Bahammam | A61M 16/0875 |
| 2018/0133426 | A1 * | 5/2018 | Hallett | A61M 16/0644 |

FOREIGN PATENT DOCUMENTS

| | | | |
|---|---|---|---|
| WO | 2006074516 | | 7/2006 |
| WO | WO 2010/067237 | A2 | 6/2010 |
| WO | WO 2011/003130 | A1 | 1/2011 |
| WO | WO 2011/142678 | A1 | 11/2011 |
| WO | WO 2012/109704 | A1 | 8/2012 |
| WO | 2016041019 | A1 | 3/2016 |
| WO | WO 2016/072868 | A1 | 5/2016 |

* cited by examiner

VENT FOR A COMPONENT OF A RESPIRATORY THERAPY SYSTEM

BACKGROUND OF THE INVENTION

Field of the Invention

The present invention generally relates to a vent for use with, or comprising part of, a component of a respiratory therapy system, for venting gases from the patient interface. The present invention stems from work based on the disclosure of our earlier application WO2014129913, the entire contents of which are incorporated herein by reference.

Description of the Related Art

One example of use of a respiratory therapy system is for the treatment of obstructive sleep apnea (OSA) by continuous positive airway pressure (CPAP) flow generator systems involves the continuous delivery of pressurized gases to the air-ways of a human via a conduit and a patient interface. Such a patient interface may be any one of the following:

- a nasal interface configured to seal around the nares or nose of the patient;
- an oral mask configured to seal around the mouth of the patient; or
- a full face mask configured to seal around both the mouth and nose of the patient.

Typically the patient interface creates at least a substantial seal on or around the nose and/or the mouth. As the patient breathes, carbon dioxide gases from expiration can progressively accumulate in the patient interface, which if left over a period of time, can become hazardous to the patient.

One solution to address or at least alleviate this issue is to provide a washout vent, also known as a bias flow vent, which enables a flow of exhaust gases to be exhausted to the atmosphere and which can provide a mechanism for reducing or removing the accumulation of carbon dioxide gases from the patient interface.

The vent, while providing a mechanism for removing carbon dioxide, can also have disadvantages. The vent can sometimes create a disturbance for the patient and/or the patient's bed partner. This disturbance typically manifests itself in two forms: noise and the creation of an air draft.

It has previously been noted that air drafts/airflow can be minimised by spacing individual vent holes of the vent further apart so that there is less entrainment of air and turbulence. At the same time, it can be desirable to reduce the overall size of a patient interface to make it less invasive for the patient and improve comfort. However, a reduced size of patient interface results in less space for vent holes and therefore the spacing between vent holes needs to be decreased. To try to minimise the size of the patient interface whilst also minimising noise and/or air drafts can be difficult.

There can also be considerations regarding the process of manufacturing a patient interface with a vent. When moulding a plurality of relatively small vent holes in close proximity to each other it is desirable for the vent holes to have a common draw direction such that they can be formed by a simple open-shut mould tool. Having a single draw direction in combination with straight holes on a flat vent surface results in any air passing through the vent holes being directed in a single direction, which may result in a concentrated airflow in a given direction, and/or increased air draft in that direction. It could be desirable for every vent hole to have a different draw plane in order to angle the airflow from a given vent hole away from that of other vent holes. However this may be impractical for tooling, especially for relatively small components.

SUMMARY OF THE DISCLOSURE

It is an object of the present disclosure to provide an improved vent for use with, or comprising part of, a component of a respiratory therapy system, for venting gases from the patient interface, and/or that will at least provide the public or the medical profession with a useful choice.

Accordingly in one aspect the invention may broadly be said to consist in a vent for venting exhaust gases from a component of a respiratory therapy system, the vent comprising:

a) a substrate having an inner surface and an outer surface, b) at least one vent hole extending through the substrate and having a vent hole circumference, the vent hole comprising an exhaust gas inlet at the inner margin of the substrate and an exhaust gas outlet at an outer margin of the substrate, the vent hole further comprising a sidewall extending between the exhaust gas inlet and the exhaust gas outlet, c) the exhaust gas inlet and the exhaust gas outlet having different diameters such that the sidewall of the vent hole is inclined at an angle of inclination between the exhaust gas inlet and the exhaust gas outlet; wherein d) the angle of inclination of the inclined side wall of the vent is non-constant around the vent hole circumference.

The vent may comprise a plurality of vent holes, and in one example comprises ten or more vent holes.

The vent holes may have the same draw direction, the draw direction being the direction at which a mould tool is opened or removed relative to the vent during manufacture. The draw direction may be substantially perpendicular to the inner surface of the vent, at a midpoint of the vent.

At least one vent hole may have a different draft direction from at least one other vent hole, the draft direction being the (resultant, average) direction that exhausted air flows out of the vent hole and defined by an axis that extends through the centre of the exhaust gas inlet and through the centre of the exhaust gas outlet of the vent hole.

The vent substrate may comprises a substantially planar substrate portion and/or a substantially arcuate substrate portion, the vent holes being spaced apart on either substrate portion.

The curvature of the arcuate substrate portion may increase away from a centre of the vent. The arcuate substrate portion may be curved in two or three dimensions. The arcuate substrate portion may be curved transversely across the vent, that is, when the vent is viewed in transverse cross section. The vent holes may be spaced transversely across the vent, with each vent hole having a different draft direction, when viewed in transverse cross section. The vent holes may be spaced longitudinally along the vent, with each vent hole having the same draft direction, when viewed in longitudinal cross section.

Each vent hole may have a different draft direction from each other vent hole. At least one vent hole may have a draft direction which is inclined relative to the draw direction, the draw direction being the direction at which a mould tool is opened or removed relative to the vent during manufacture. The draft direction may be inclined relative to the draw direction, when the vent hole is viewed in transverse cross section. The draft direction may be inclined relative to the draw direction, when the vent hole is viewed in longitudinal cross section.

The angle of inclination of the draft direction relative to the draw direction when the vent hole is viewed in transverse cross section may be different from the angle of inclination of the draft direction relative to the draw direction when the vent hole is viewed in longitudinal cross section.

The vent hole(s) further from the centre of the vent may have a draft direction which is inclined at a greater angle from the draw direction relative to the vent hole(s) nearer the centre of the vent.

The vent area may be less than approximately 500 $mm^2$, less than approximately 450 $mm^2$, and in one example may be substantially equal to or less than approximately 400 $mm^2$.

The taper angle of one vent hole may be different from the taper angle of another vent hole. The taper angle of the vent hole(s) furthest from a centre of the vent may be greater than the taper angle of the vent hole(s) nearer the centre of the vent.

At least one vent hole may have sidewalls which are asymmetric, when each vent hole is viewed in transverse cross section.

The taper angle of the sidewall of a vent hole that is furthest from the centre of the vent when that vent hole is viewed in transverse cross section may be greater that the taper angle of the sidewall of that vent hole that is closest to the centre of the vent.

The centre of the exhaust gas outlet may be offset from the centre of the exhaust gas inlet, when the vent is viewed in plan.

The exhaust gas outlet and the exhaust gas inlet may be non-concentric.

The exhaust gas inlet and/or the exhaust gas outlet of at least one vent hole may be radiused. The radius may be asymmetric, when that vent hole is viewed in transverse cross section. In some examples, the exhaust gas outlet may be radiused, such that the exhaust gas outlet is of larger diameter than the exhaust gas inlet. In other examples, the exhaust gas inlet is radiused, such that the exhaust gas inlet is of larger diameter than the exhaust vent outlet.

The vent holes may be arranged in a plurality of vent hole arrays, each array having at least one vent hole, the vent hole of one array having at least one characteristic which is different from a vent hole in at least another array.

At least one array may differ from at least another array in respect of one or more of the following:

a) vent hole having a different draw direction;
b) vent hole having a different draft direction;
c) vent hole having a different exhaust gas outlet shape and/or diameter;
d) vent hole having a different exhaust gas inlet shape and/or diameter;
e) vent hole side walls having differing taper angles;
f) vent hole having different radiusing/chamfering of the exhaust gas outlet and/or the exhaust gas inlet; and/or
g) different number of vents.
h) different spacing of vents;
i) different pattern of vents; and/or
j) different length of each vent hole.

In some examples, the vent array may have the following properties:

a) the number of vent holes may vary between 2 to 100, and in one example there may be 36 vent holes;
b) each vent hole may have a diameter between 0.1 and 2 mm, and in one example may have a diameter of 0.75 mm;
c) the thickness of the substrate may vary between 0.1 mm and 10 mm and in one example may be 1 mm;
d) the spacing between adjacent vent holes can vary according to the location of each vent hole within the vent and may be between 0.5 mm and 5 mm, and in one example is approximately 3.87 mm; and/or
e) The taper angles β+ and β− may each be between −25° and +25°, and in one example may be substantially 10° and −10° respectively.

The vent geometry may be configured in accordance with any one or more of the following predetermined relationships:

a) number of vent holes relative to vent area;
b) diameter of each vent hole relative to vent area;
c) diameter of each vent hole relative to the number of vent holes;
d) vent hole diameter relative to any one or more of: substrate thickness and/or the angle of inclination of the vent hole side walls, curvature of the substrate;
e) the angle of inclination of the vent hole side walls relative to any one or more of: the curvature of the substrate, the vent area, the diameter of each vent hole, the spacing between each vent hole, the number of vent holes and the substrate thickness;
f) geometry of the vent holes, such as angle of inclination of the side walls, with respect to the draw angle and/or surface curvature (or lack of) of the substrate;
g) ratio of vent hole diameter to substrate thickness;
h) ratio of vent hole diameter to number of vent holes; and/or
i) ratio of number of vent holes to substrate thickness.

According to another aspect of the invention there is provided a vent for venting exhaust gases from a component of a respiratory therapy system, the vent comprising:

a) a substrate having an inner surface and an outer surface,
b) at least one vent hole extending through the substrate, the vent hole comprising an exhaust gas inlet at the inner surface of the substrate and an exhaust gas outlet at an outer surface of the substrate, the exhaust gas inlet and the exhaust gas outlet each having a respective centre,
c) the exhaust gas inlet and the exhaust gas outlet defining a draft direction being the direction that exhausted air flows out of the vent hole and which is defined by an axis that extends through the centre of the inlet and the centre of the outlet of the vent hole, wherein
d) the draft direction of the vent hole is not aligned with a draw direction, the draw direction being the direction at which a mould tool is opened or removed relative to the vent during manufacture.

According to a further aspect of the invention there is provided a vent for venting exhaust gases from a component of a respiratory therapy system, the vent comprising:

a) a substrate having an inner surface and an outer surface,
b) at least one vent hole extending through the substrate, the vent hole comprising an exhaust gas inlet at the inner surface of the substrate and an exhaust gas outlet at an outer surface of the substrate, the exhaust gas inlet and the exhaust gas outlet each defining a respective centre,
c) the centre of the exhaust gas inlet being offset from the centre of the exhaust gas outlet, when the vent is viewed from above.

According to another aspect of the invention there is provided a vent for venting exhaust gases from a component of a respiratory therapy system, the vent comprising:

a) a substrate having an inner surface and an outer surface,
b) at least two vent holes extending through the substrate and each having a circumference, an exhaust gas inlet at the inner surface of the substrate and an exhaust gas outlet at an outer surface of the substrate, a sidewall being defined between the exhaust gas inlet and the exhaust gas outlet of each vent hole,
c) the exhaust gas inlet of each vent hole having a different diameter to the diameter of the exhaust gas outlet of that vent hole such that the sidewall of each vent hole is inclined at an angle of inclination between the exhaust gas inlet and the exhaust gas outlet; wherein
d) the angle of inclination of the inclined side wall of one vent hole is different from the angle of inclination of the side wall of another vent hole.

According to yet further aspect of the invention there is provided a vent for venting exhaust gases from a component of a respiratory therapy system, the vent comprising:

a) a substrate having an inner surface and an outer surface,
b) at least two vent holes extending through the substrate, each vent hole comprising a bore extending through the substrate, the bore comprising an exhaust gas inlet at the inner surface of the substrate and an exhaust gas outlet at an outer surface of the substrate, the exhaust gas inlet and the exhaust gas outlet each defining a respective centre,
c) the exhaust gas inlet and the exhaust gas outlet of each vent hole defining a draft direction being the direction that exhausted air flows out of that vent hole and defined by an axis that extends through the centre of the inlet and through the centre of the outlet of that vent hole, wherein
d) the draft direction of one vent hole is different to the draft direction of the other vent hole.

According to another aspect of the invention there is provided a vent for venting exhaust gases from a component of a respiratory therapy system, the vent comprising:

a) a substrate having an inner surface and an outer surface,
b) at least one vent hole extending through the substrate and having a circumference, the vent hole comprising an exhaust gas inlet at the inner surface of the substrate and an exhaust gas outlet at an outer surface of the substrate, a sidewall being defined between the exhaust gas inlet and the exhaust gas outlet,
c) the exhaust gas inlet having a different diameter to the diameter of the exhaust gas outlet such that the sidewall of the vent hole is inclined at an angle of inclination between the exhaust gas inlet and the exhaust gas outlet; wherein
d) the angle of inclination of the inclined side wall of the vent is non-constant with respect to a draw direction, the draw direction being the direction in which a mould tool is opened or removed during manufacture of the vent.

According to another aspect of the invention there is provided a patient interface comprising the vent of any one of the above statements.

The patient interface may be any one of:

a) a nasal interface configured to seal around the nares or nose of the patient;
b) an oral mask configured to seal around the mouth of the patient; or
c) a full face mask configured to seal around both the mouth and nose of the patient.

According to another aspect of the invention there is provided a component of a respiratory therapy system comprising the vent of any one of any one of the above statements.

The component may comprise any one of:

a) an elbow connector configured to connect a gas delivery conduit to a patient interface;
b) a gas delivery conduit;
c) a gas delivery conduit connector configured to connect a gas delivery conduit to another component of the respiratory therapy system.

According to another aspect of the invention there is provided a respiratory therapy system comprising the vent of any one of the above statements and any one or more of:

a) a breathing gas flow generator;
b) a breathing gas humidifier;
c) a gas delivery conduit, which may or may not be heated; and/or
d) a patient interface.

Throughout this specification the following terms have the following meanings:

'Draft direction': is the direction that the exhausted air flows out of the vent hole or holes, and is defined by an axis that extends through the centre of the inlet and outlet of the or each hole. References to 'draft direction' herein refer to the average or resultant direction of exhausted air from the vent, averaged across the width of the vent.

'Draw direction': is the direction at which a mould tool is opened or removed relative to the component being moulded.

'Taper angle': is the angle formed between the wall of a vent hole and the draft direction.

Further aspects of the invention, which should be considered in all its novel aspects, will become apparent from the following description.

DESCRIPTION OF THE DRAWINGS

A number of embodiments of the invention will now be described by way of example with reference to the drawings in which.

DETAILED DESCRIPTION

Figure 1:
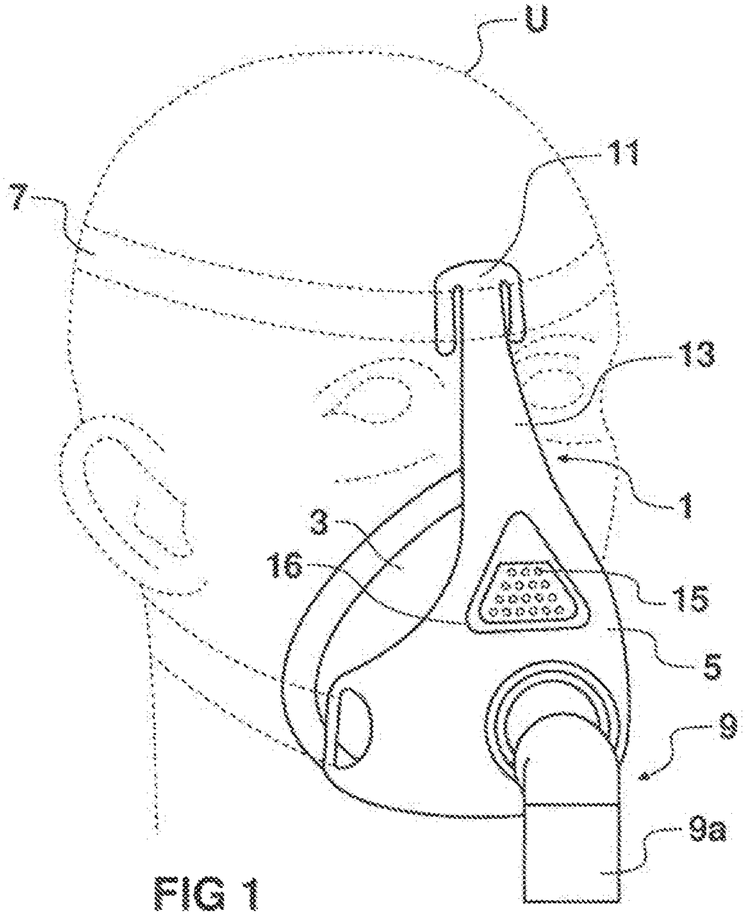
FIG. 1 is a perspective view of a respiratory therapy system component being a patient interface on a patient's head, the patient interface incorporating a vent having a plurality of vent holes, the vent being in accordance with the present invention.

With reference initially to FIG. 1, an embodiment of a patient interface 1 is illustrated on a user U, the patient interface 1 incorporating a vent in accordance with the present invention. The interface 1 can be used in the field of respiratory therapy and therefore in any respiratory treatment, respiratory assistance, resuscitation or ventilation system. In some embodiments, the interface 1 has particular utility with forms of positive pressure respiratory therapy. For example, the interface 1 can be used for administering continuous positive airway pressure ("CPAP") treatments, variable positive airway pressure ("VPAP") treatments and/or bi-level positive airway pressure ("BiPAP") treatments. The interface 1 can be compatible with one or more different types of suitable CPAP systems.

The interface 1 can comprise any of a plurality of different types of suitable mask configurations. For example, certain features, aspects and advantages of the present invention can be utilized with nasal masks, full face masks, oronasal masks or any other positive pressure mask. Although the illustrated prior art mask is a full face mask, the scope of the present disclosure should not be limited by the particular embodiments described.

In the illustrated configuration, the interface 1 comprises a mask body 3, a mask frame 5 and a connection port assembly 9. The mask body 3 is configured to cover the user's mouth and/or nose to deliver respiratory gases to the user. The mask body 3 can be secured to the mask frame 5. The mask frame 5 is held in place by a headgear assembly 7 that wraps around a part or parts of the user's head. The connection port assembly 9 can be connected to the mask body 3 and/or mask frame 5, preferably with a releasable connection. In some configurations, the connection port assembly 9 can include a ball joint to improve flexibility and comfort. The connection port assembly 9 in this example comprises an elbow connector 9A configured to be connected between the mask body 3 and/or mask frame 5 and a gas delivery conduit (not shown).

The mask frame 5 can couple to the mask body 3 and help stabilize the interface 1 on the user's face. The mask frame 5 can be any shape and size to functionally secure the interface 1 to the user's face. The mask frame 5 can be attached to the mask body 3 with interlocking clips, tabs or other functional couplers. The mask frame 5 can be rigid, substantially rigid or semi-rigid to provide support for the mask body 3. For example, the mask frame 5 can be at least partially made of a metal or rigid plastic, such as acrylic, polycarbonate or high-density polyethylene.

As illustrated in FIG. 1 the mask frame 5 can extend to the user's forehead and may optionally include a forehead rest 11. The forehead rest 11 can help stabilize the interface 1 to the user's face by providing a support point for the interface 1 and connection points for the headgear assembly 7. In the illustrated configuration, a frame bridge 13 extends between the main body of the frame 5 and the forehead rest 11. The frame bridge 13 can be integrally formed or moulded with the rest of the mask frame 5 from the same rigid material.

In some configurations, the forehead rest 11 can be a separate flexible piece that is attached or overmoulded onto the mask frame 5. For example, the forehead rest 11 can be made of a flexible silicone that is overmoulded onto the frame bridge 13. The flexible material advantageously conforms to the user's forehead anatomy and helps improve comfort to the user with soft material contact. In some configurations, the forehead rest 11 can be attached or integrally formed as part of the mask frame 5 and can be made of the same material as the mask frame 5 and frame bridge 13.

The typical method of passively venting carbon dioxide (C02) and expiratory gases is via the use of a vent comprising a vent hole or a vent hole array that is incorporated into the mask body or gas path componentry that, for example, is directly connected to the mask. In the embodiment illustrated in FIG. 1, the interface 1 has a vent 15 for expelling gases from inside the mask to the environment. The vent 15 can help expel carbon dioxide gases from the user to reduce the rebreathing of the carbon dioxide gases. In other embodiments, the vent may be provided in the connection port assembly 9, for example on the elbow connector.

The vent 15 creates a controlled or known leak to enable the exhausting of the user's exhaled carbon dioxide gases. There may be a performance trade-off between the location of the vent 15 (relative to the patient's mouth or nose) and the amount of bias flow required. As used herein, bias flow refers to the flow of gases to the environment through the vent holes of the vent. The flow rate of the bias flow and the design geometry of the vent holes can have an effect on the noise level and draft that the bias flow produces, as well as the amount of entrainment that the exiting gas flow may cause, as discussed further below.

In the illustrated configuration, the vent 15 comprises a plurality of vent through holes on the mask body 3 that expel gases through a cut-out 16 in the mask frame 5. In other configurations, the vent 15 can comprise slits or large openings instead of or in addition to small through holes. In some configurations, the vent 15 can be disposed on other portions of the interface, such as the connection port assembly 9 or connection joints, as discussed below. Generally, relatively smaller vent hole sizes produce less airflow noises compared to a larger vent hole size given the same flow velocity through both hole sizes. The plurality of vent holes helps reduce airflow noises compared to having one or a few holes with the same vent area when expelling a given volume of gas.

In some embodiments, the vent 15 can be formed as a separate component/module from the mask body 3 or mask frame 5. The separate vent module can be permanently or releasably assembled to the mask body 3 or mask frame 5. For example, the vent module can have threads that mate with complementary threads on the mask body 3. In other configurations, the air vent module can have any type of functional coupler or connector to mate the vent module to the mask body 3 or mask frame 5. The vent module may connect with the mask body 3 or mask frame 5 via a snap fit connection for example. In these configurations, the vent module can be removed easily for service, cleaning or replacement.

The vent module can be overmoulded to the mask body 3 or mask frame 5 for a permanent attachment. The over-moulding can include a flexible gusset between the vent module and the mask that helps with flexibility. In other configurations, the vent module can be permanently attached using, for example, adhesives or ultrasonic welding.

Furthermore, the vent 15 can be formed of a different material than the mask body 3 or mask frame 5. This can advantageously allow the vent 15 to be made of a material that is suitable for forming vent holes or apertures. For example, the vent 15 can be made of a soft and/or flexible material while the mask body 3 and/or mask frame 5 are made of a more rigid material. In some configurations, the soft and/or flexible material (e.g., silicone, rubber, foam and the like) may help reduce the amount of noise the flow makes through the vent holes. However, in some embodiments, the vent 15 can be formed of the same material as the mask body 3 and/or mask frame 5 while providing acceptable noise and draft levels.

A separate vent module advantageously allows improved manufacturing and product quality. By having the vent 15 in a separate component, the moulding of the small and detailed vent holes can be better controlled. By moulding the vent 15 as a separate component, the part tolerances can be better controlled and result in more consistent hole dimensions having a more consistent flow rate performance between parts. Moulding a separate vent module may allow for production of more complex vent designs as a result of not having to accommodate undercuts and other geometric restrictions of other components, such as the mask body 3 for example. Improved control of the part dimensions may also improve control of noise levels, such as by controlling the part contours to produce a smooth air-flow through the vent holes.

It has been determined that optimizing the design of the vent hole geometry and the adjoining plenum chamber can be beneficial in reducing the noise and draft levels of the fluids exiting the vents. Various definitions can be used to quantify or measure sound levels.

First, sound power can be used to quantify the sound levels. This is the measure of the amount of energy from a particular sound source. The measurement is independent of distance from the sound source. Second, sound pressure can be used to quantify sound levels. This is the measure of the intensity of the sound at a particular distance from the sound source. This is typically measured in decibels (i.e., dB or dBa). A third method of quantifying sound levels is a sound field. A sound field is a graphical representation (i.e., a contour map) of the pressure levels of a particular sound as a function of position from the sound source.

Figure 2:
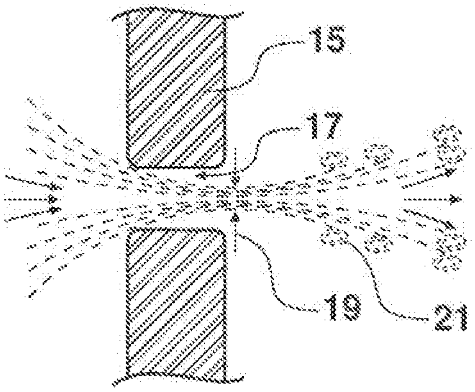
FIG. 2 is a sectional side view through a prior art vent, showing an example fluid flow through a vent hole.

FIG. 2 illustrates an example of a fluid flow passing through a vent hole 17 of vent 15. As used herein, the term fluid is used to refer to liquids, gases or a combination of liquids and gases. During the process of flowing through the vent hole 17 a complex set of fluid dynamics occurs, for which there is considerable digital and experimental based data sets to describe its behaviour.

When a fluid flow experiences a sudden contraction in the flow path, such as with vent holes, the flow contracts through a minimum cross-section called the vena contracta 19, as illustrated in FIG. 2. The position of the vena contracta 19 is downstream of the vent hole 17 entrance. Substantially all the fluids that pass through the vent hole 17 will pass through the vena contracta 19 and this location is also the location of highest flow velocity and lowest pressure.

As the fluid flow exits the vena contracta 19, it progressively reduces in velocity and increases in pressure, until it reaches a velocity of approximately zero and a pressure of approximately atmospheric pressure. In this transition zone after the vena contracta 19, vortices 21 may form at the boundary between the exiting fluid flow and the stationary atmospheric air, which are caused by viscous effects between the two fluids being at different velocities. This effect is known as vortex shedding. At a macro level, the vortex shedding may produce rapid random fluctuations which occur across a range of frequencies. Typically, the frequencies can range from at least approximately 1 kHz to less than or equal to 10 kHz, with wavelengths in the range of at least approximately 1 mm to less than or equal to 4000 mm.

There are a number of geometric factors that influence the amount of sound energy created by the vortex shedding. These geometric variables can be utilised during the design of the vent holes 17 to reduce and minimise the amount of sound energy created when fluids travel through the vents holes 17. These variables can include:

- The flow rate through the vent hole 17 which is a function of the hole diameter and the pressure drop from the exhaust gas inlet to the exhaust gas outlet of the vent hole 17;
- The quality of the vent hole 17, which can be characterised by the smoothness of the vent hole 17 and the absence of debris in the vent hole 17;
- The geometry of the vent hole 17, particularly the entrance radius and exit radius of the vent hole 17, if any, and the hole length to hole diameter ratio of the vent hole 17;
- The geometry of the vent hole array, for example the hole pitch (i.e., the distance between vent holes 17).

The two most commonly understood flow types are laminar flow and turbulent flow, which can be quantified by a Reynolds number. For design purposes, the Reynolds number at which the transition between laminar flow and turbulent flow occurs is approximately 2300. In situations where turbulent flow occurs at the vena contracta, there is usually an increase in sound level. Furthermore, when debris or surface imperfections exist in the vent holes 17, this can create a mechanism that promotes an earlier transition from laminar flow to turbulent flow compared to smooth surface vent holes.

Being able to adjust the geometry of the vents offers the ability to control the sound levels produced by the vents to be within an acceptable range for use as part of a CPAP system. Some design envelopes have been developed that achieve acceptable sound levels. One of the design envelopes is for the vent hole diameter versus the exit radius.

As noted above, aside from the performance of the vent 15 in use, there can also be considerations to be taken into account regarding the process of manufacturing a patient interface with a vent having vent hole or holes. When moulding a plurality of relatively small vent holes in close proximity to each other it is desirable for the vent holes to have a common draw plane such that they can be formed by a simple open-shut mould tool.

Figure 3A:
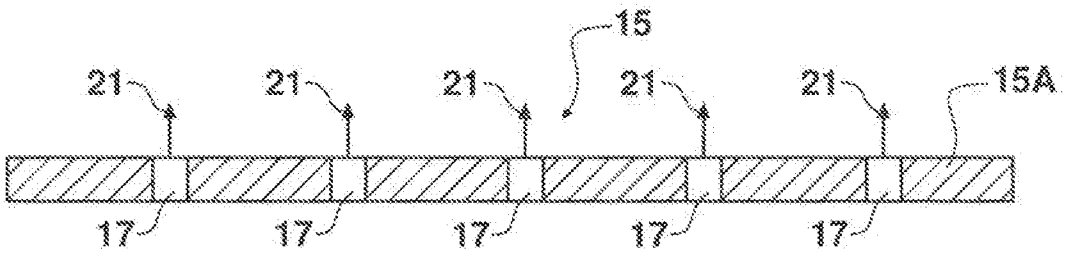
FIGS. 3*a* to 3*d* are sectional side views of prior art vents indicating the draft direction and draw direction.
Figure 3B:
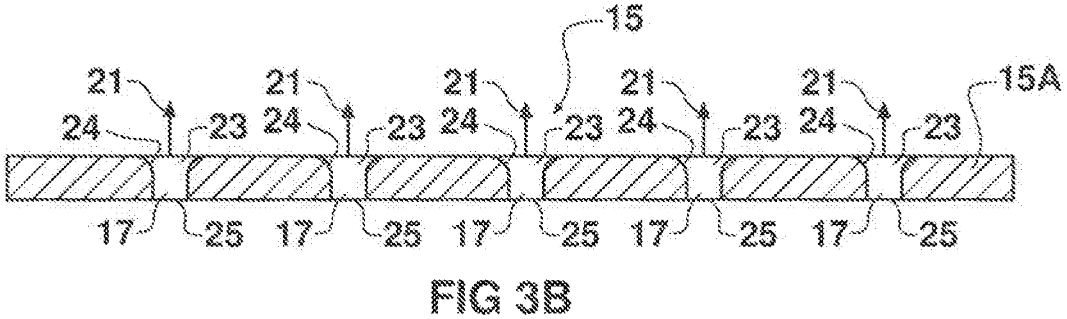
Figure 3C:
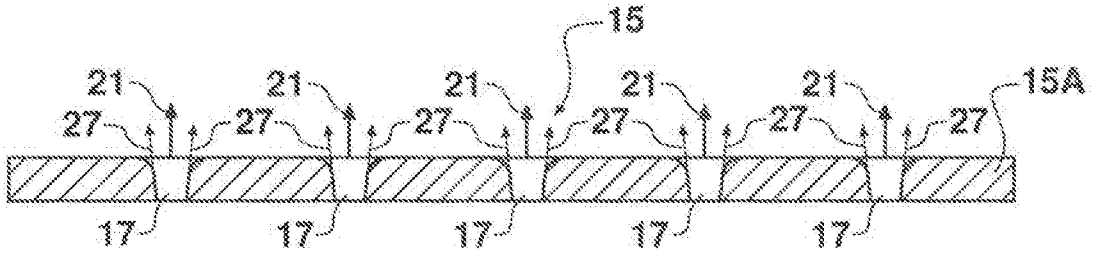
Figure 3D:
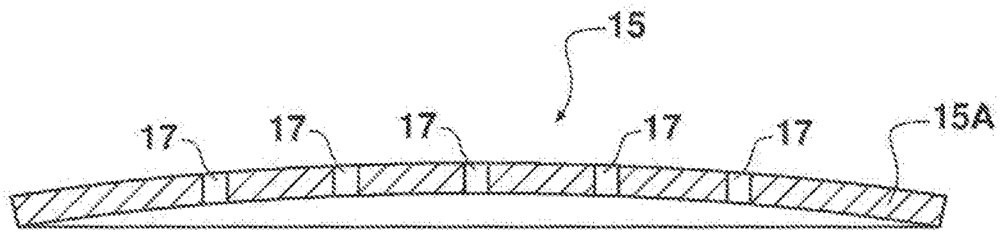

With additional reference to FIGS. 3A-3D, the prior art vent 15 may take a number of forms, each having a single draw plane or direction. FIG. 3*a* shows a vent 15 comprising a planar substrate 15A provided with a plurality of straight, parallel walled vent holes 17. The arrows 21 indicate a common draft direction and draw direction. FIG. 3*b* shows a vent similar to that of FIG. 3*a* but where an exhaust gas outlet 23 of each vent hole 17 is radiused 24. Again the arrows 21 indicate a common draft direction and draw direction. FIG. 3*c* shows a further prior art variant where the side walls of each vent hole 17 are tapered or inclined, so that the exhaust gas outlet 23 has a larger diameter than the exhaust gas inlet 25. In such a configuration, the arrows 21 indicate the common draw direction. The average, draft direction resultant from the exhaust gases flow across the width of each vent hole 17 is the same direction as the draw direction, with the arrows 27 indicating the draft angle over which the exhaust gasses flow is dispersed. Finally, FIG. 3*d* shows a variant of the prior art vent of FIG. 3*a*, but where the vent 15 comprises an arcuate substrate 15A.

Figure 4:
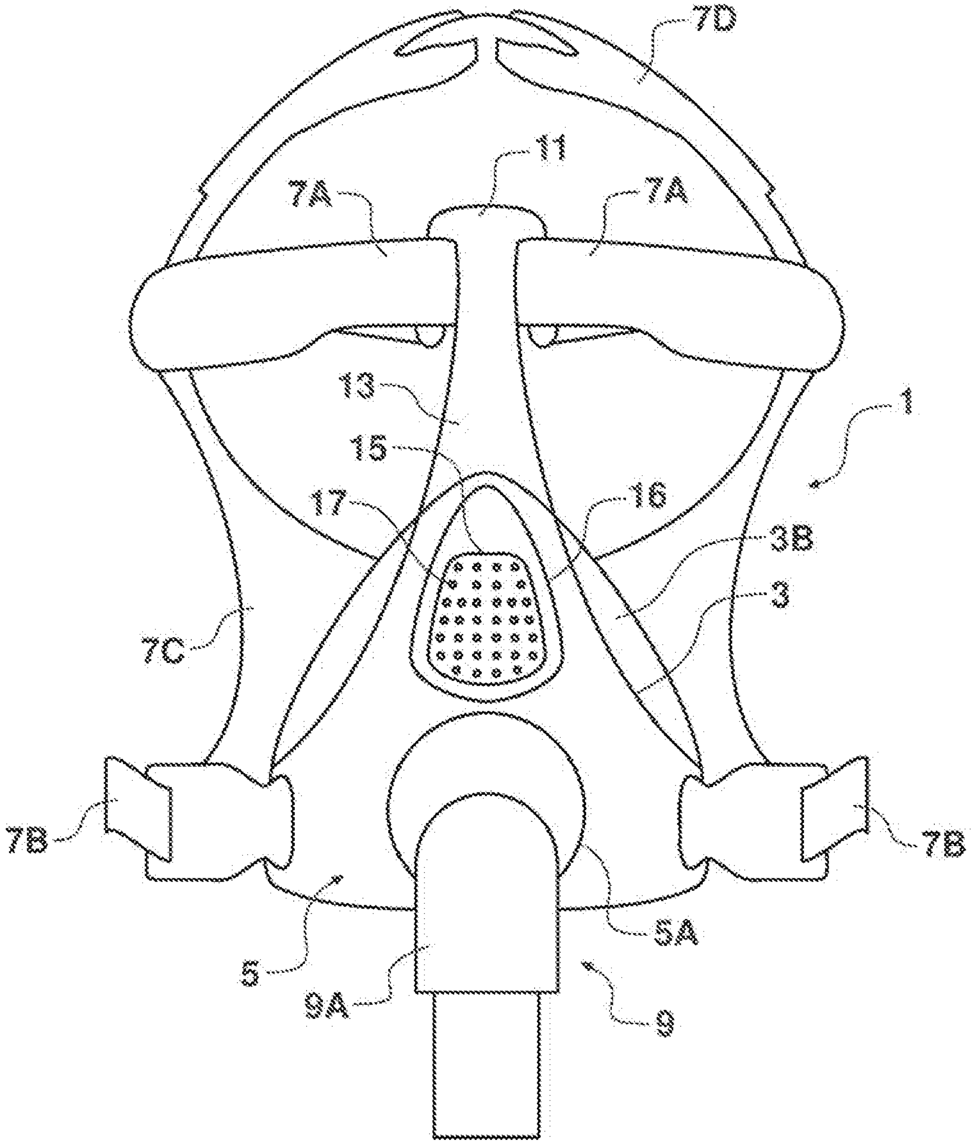
FIG. 4 is a front view of a prior art patient interface incorporating a vent having a plurality of vent holes.

With additional reference to FIG. 4, mask assembly 1 is shown in more detail. The mask body 3 is formed with an integral vent 15 comprising a vent array of a plurality of vent holes 17. The vent 15 is aligned with, and may protrude through, cut-out 16 in the mask frame 5. The mask body 3 comprises a rigid shell (which cannot be clearly seen in FIG. 4) and a soft silicone cushion 3B, overmoulded onto the shell 3A. The cushion 3B seals against the face of the user. In this example, the connection port assembly 9 comprises an elbow connector 9A configured to be connected between the mask body 3 and a gas delivery conduit (not shown). The elbow connector 9A projects through a suitable opening 5A formed in the mask frame 5.

In this example headgear assembly 7 comprises a pair of upper side straps 7A extending from forehead rest 11, a pair of lower side straps 7B extending from lateral parts of the mask frame 5, a rear strap 7C which joins the upper and lower side straps 7A, 7B, at the rear of the head of the user, and a crown strap 7D which extends over the crown of the head of the user, from each upper side strap 7A. Suitable connectors, such as incorporating hook and loop fasteners, may be provided to secure the headgear 7 to the mask frame 5 and forehead rest 11. Any or all of the above straps may include adjusters, such as buckles, configured to enable the length of the strap(s) to be adjusted. Any one or more of the straps may be elastic or inelastic or comprise portions that are elastic or inelastic. Any one or more the straps may comprise more rigid portions, for example, to help maintain a desired shape of the headgear 7.

Figure 5A:
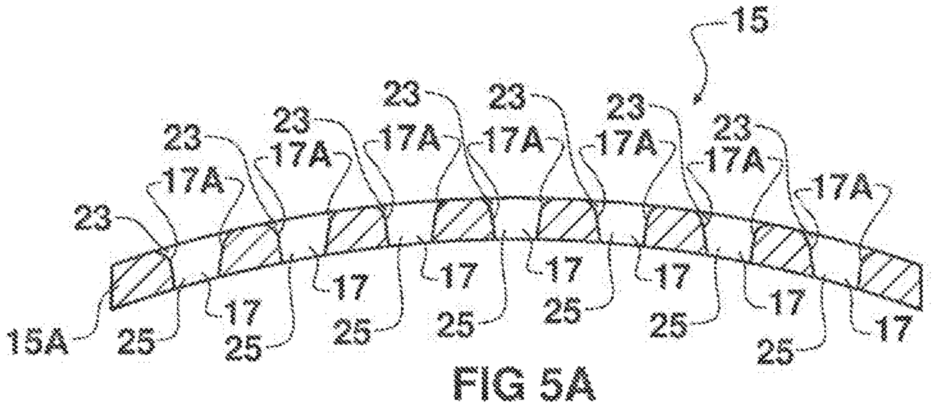
FIGS. 5*a* and 5*b* are sectional side views of the vent of the prior art patient interface of FIG. 4.
Figure 5B:
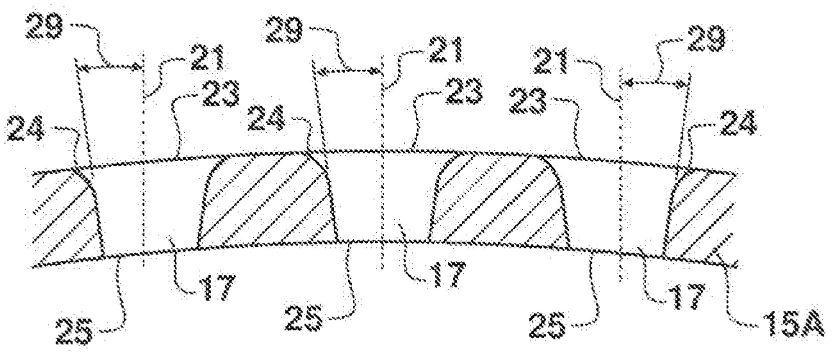

The vent 15, with additional reference to FIGS. 5A and 5B, comprises an arcuate substrate 15A provided with a vent array of a plurality of vent holes 17 the side walls 17A of which are tapered or inclined, so that the exhaust gas outlet 23 has a larger diameter than the exhaust gas inlet 25. The exhaust gas outlet 23 of each vent hole 17 is also radiused 24. As per the example of FIG. 3*c*, the average, resultant draft direction of each vent hole 17 is the same as the draw direction 21. Further, the side walls 17A have a taper angle 29, relative to the draw direction 21 of around 10°. In this example the diameter of the exhaust gas inlet 25 is approximately 0.75 mm, and the exhaust gas outlet 23 incorporates a 0.5 mm radius.

Figure 6:
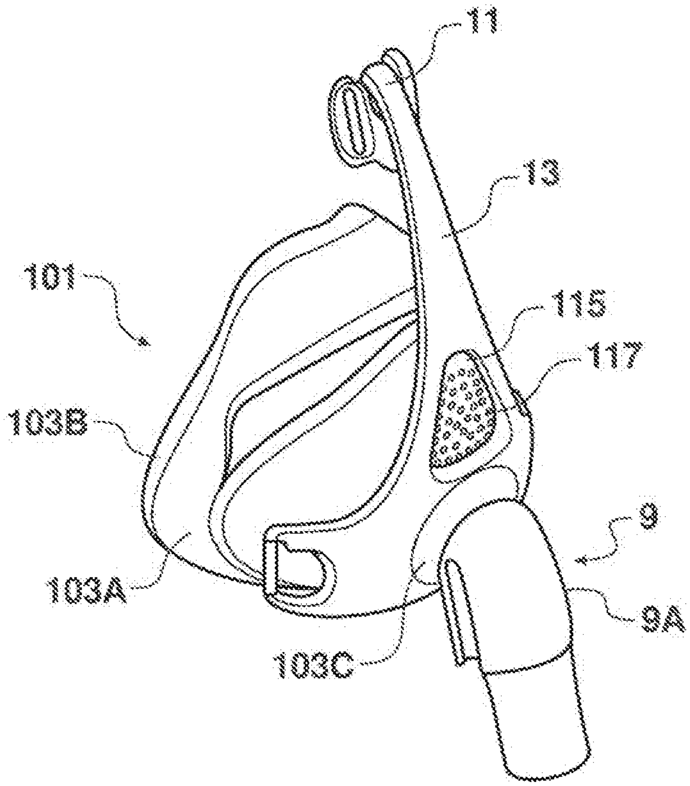
FIG. 6 is a perspective view of a patient interface assembly incorporating a vent in accordance with the present invention.
Figure 7:
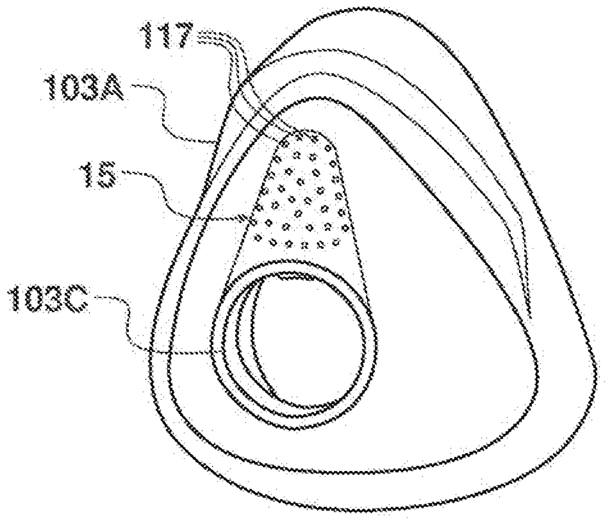
FIG. 7 is a perspective view of a patient interface comprising part of the patient interface assembly of FIG. 6.

With reference to FIGS. 6 to 8, a patient interface assembly 101 incorporating a vent 115 in accordance with the present invention comprises many features that are identical or similar to those of prior art patient interface 1 described above with reference to FIGS. 1 to 5. Like features have been given like references.

Vent 115 comprises an arcuate vent substrate 115A which forms an integral part of the rigid mask shell 103A, above a gas inlet aperture 103C, into which the connection port assembly 9 (not shown) is received and connected to deliver breathable gas to the plenum chamber defined by the mask shell 103A. In this example, the vent substrate 115A is substantially contiguous with, and does not protrude from, the outer surface of the mask shell 103A. A soft silicone cushion 103B is overmoulded onto, or otherwise connected to the mask shell 103A. The vent substrate 115A comprises an inner surface 115B, inside the plenum chamber formed by the mask shell 103A and cushion 103B, and an outer surface 115C, external of the mask shell 103A, and which is exposed to atmosphere and the external environment.

The vent array comprises a plurality of vent holes 117 having a structure and configuration which will be described in more detail below. The structure and configuration of the vent holes 117, relative to the mask shell 103A, and relative to each other, is such that exhaust gases are vented through the vent array in a frustro-conical dispersing pattern whereby as well as dispersing longitudinally outwardly from the vent 115 substantially in the direction of a notional longitudinal axis A projecting through the centre of the vent array perpendicularly to the surface of the substrate at the centre of the vent array, the exhaust gases also have a radially outward component that disperses a portion of the exhaust gases radially outwardly from the notional longitudinal axis A. Thus, at a position spaced along the longitudinal axis away from the vent array, the exhaust gases are spread over a dispersed area that is greater than the area of the vent array. This dispersed area increases as the exhaust gases move further from the vent array, such that the exhaust gases adopt a frustoconical dispersing pattern.

Figure 8A:
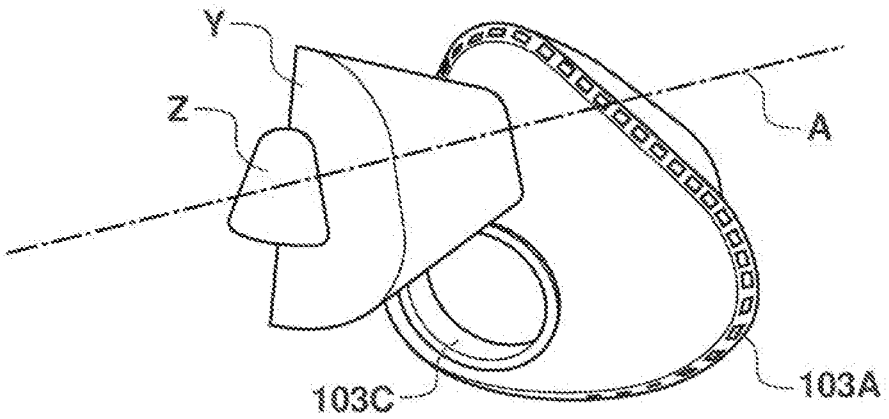
FIGS. 8*a* and 8*b* are schematic perspective views of the patient interface of FIG. 7, showing example expiratory gas flows through the vent.
Figure 8B:
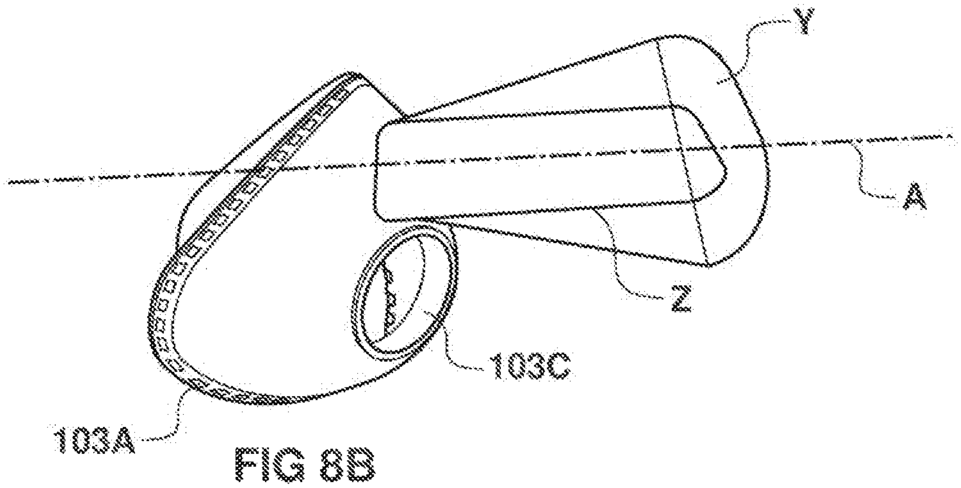

With reference to FIGS. 8A and 8B, the estimated dispersing pattern of exhaust gas from a vent 115 in accordance with present invention is approximated by the outer shaded flow path Y, with the estimated dispersing pattern of exhaust gas from a prior art vent 15 being approximated by the inner shaded flow path Z. The vent 115 thus serves to disperse the exhaust gases over a wider area than the prior art vent 15, and at a wider angle relative to the notional longitudinal axis A. This serves to reduce the velocity of the exhausted gases, the distance that the exhausted gases will travel, and the disturbance caused by the exhausted gases.

Figure 9A:
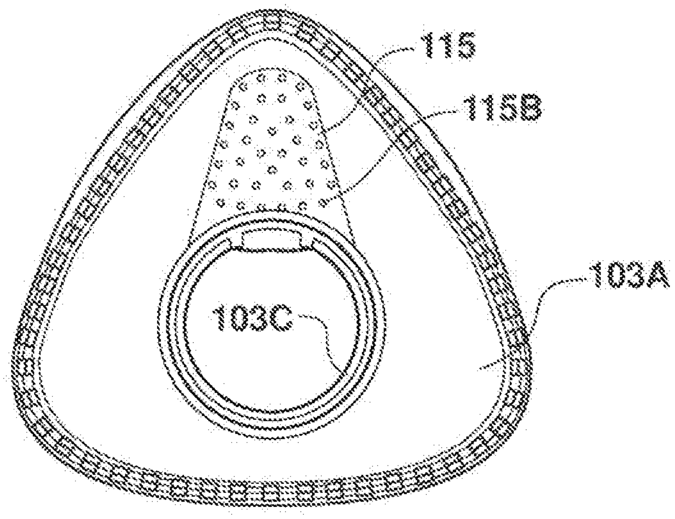
FIGS. 9*a* and 9*b* are rear views of the patient interface of FIG. 7.
Figure 9B:
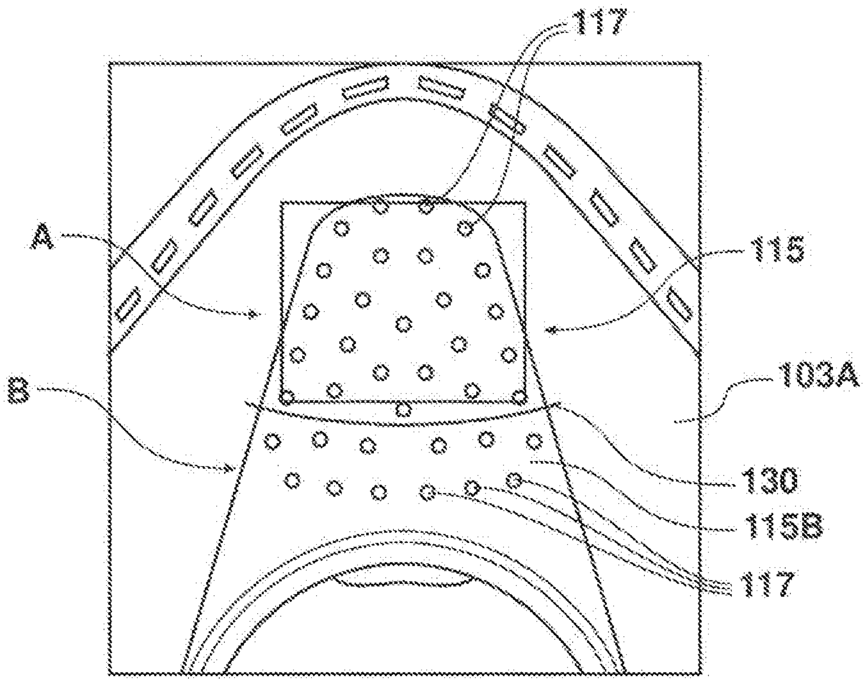

With additional reference to FIGS. 9A and 9B, the vent holes 117, in this example, are configured into two vent arrays A, B which are separated by a notional separation line 130. The vent holes 117 above the separation line 130 are formed by a sliding insert that forms part of a housing mould tool. The vent holes 117 below the separation line are formed by the main cavity of the mould tool. This configuration provides the bias vent 115 with two draw angles, which in turn increases the angle over which exhausted air is dispersed on exit from the bias vent 115. This in turn reduces the draft and noise experienced by the user and/or their bed partner.

The vent holes 117 have been arranged in a number and configuration that provides the greatest spacing between vent holes 117 for the required number of vent holes 117, within the limited space available on the vent substrate 115A. In this example there are 36 vent holes 117, each having a diameter of 0.75 mm. The number of vent holes may vary between 2 to 100. The thickness of the substrate 115A in this example is 1 mm but may vary between 0.1 mm and 10 mm. The spacing between adjacent vent holes 117 is approximately 3.87 mm, but this can vary according to the location of each vent hole 117 within the vent 115 and may be between 0.5 mm and 5 mm. It can be desirable to have the vent holes 117 spaced as far apart as possible within the confines of the number of vent holes 117 required to achieve the desired exhaust gas flow performance and the size of the vent 115 available.

The configuration of the vent holes 117 will now be described in more detail.

Figure 10A:
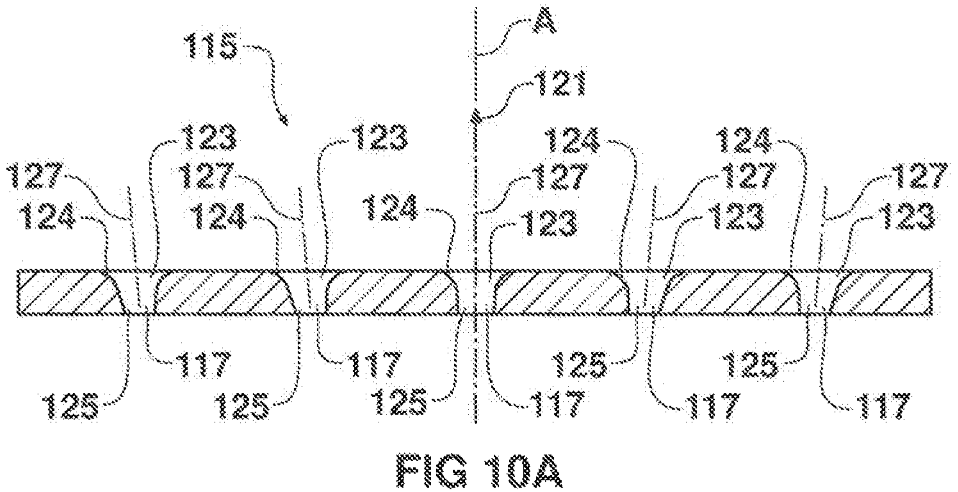
FIGS. 10*a* and 10*b* are sectional side views of a vent in accordance with the present invention, indicating the draft direction and draw direction.
Figure 10B:
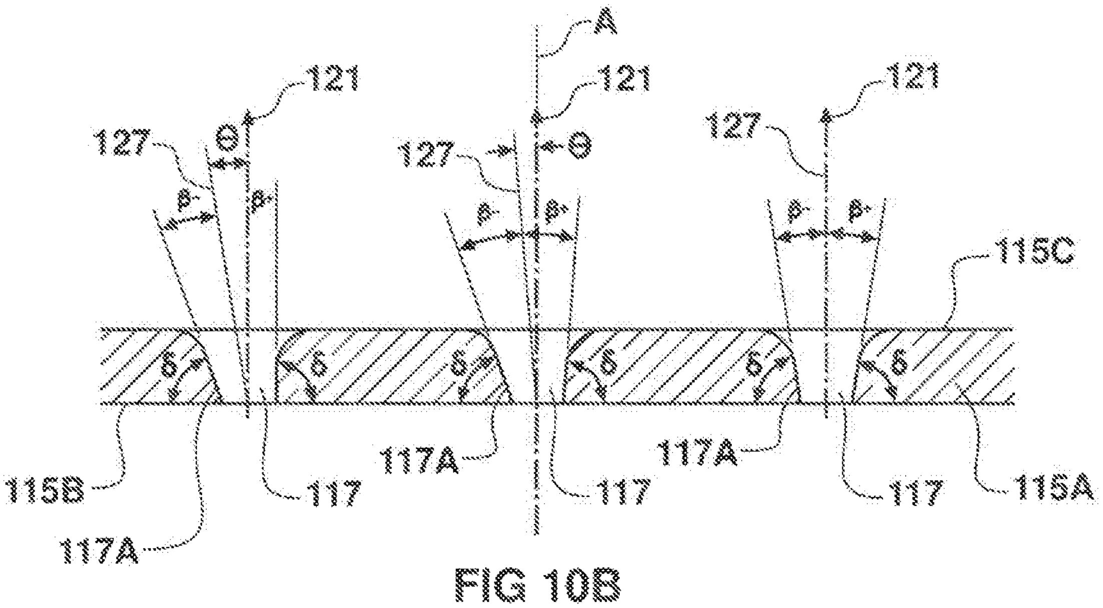

With reference to FIGS. 10A and 10B, the vent holes 117 in the vent 115 are illustrated in an example vent substrate 115A which is substantially planar.

In this example, each vent hole 117 has tapered or inclined side walls 117A, in that the side walls 117A, in transverse cross section, are angled relative to the draw direction indicated by arrow 121. The exhaust gas outlet 123 has a larger diameter than the exhaust gas inlet 125. The exhaust gas outlet 123 is radiused 124. The exhaust gas outlet 123 and the exhaust gas inlet 125 each have a notional centre point, a vent hole axis 127 passing through the notional centre point of the outlet and inlet 123, 125. This vent hole axis 127 defines the draft direction of each vent hole 117. In this example, the draft direction 127 of the middle vent hole 117, labelled hole H3, is aligned with the draw direction 121, whilst the draft directions 127 of the outer vent holes 117, labelled hole H2 and hole H3, are inclined outwardly from the draw direction 121. Thus each vent hole 117 has a common, identical draw direction 121, but a different draft direction 127, with the angle of inclination between the draft direction 127 and the draw direction 121 increasing as the vent holes 117 are further from the middle vent hole 117, hole H3. Thus, the outermost vent hole 117, hole H1, disperses the exhausted gases at a greater angle relative to the draw direction 121 and notional axis A than the innermost vent holes 117, holes H2 and H3.

The shape and configuration of vent holes 117 can be seen in more detail with reference to FIG. 10*b*. The figure above is an enlarged view of a portion of FIG. 10*a*.

The rightmost vent hole 117 (hole H3) may be centrally located within the bias vent 115 and is substantially symmetrical about the draw direction 121. The draft direction 127 is the same as the draw direction 121, at least in this cross-section plane, for central hole H3, with the taper angle of the hole side wall 117A, β−, β+ being equal for each side wall 117A.

For the outer holes, hole H1 and hole H2:

a) The draft direction 127 is offset from the draw direction 121 by an angle θ that is different for each hole 117.

b) The closer the hole to the edge margin of the bias vent 115, the greater the angle θ. This spreads the draft of air over a greater angle and reduces the likelihood of airflow from one hole 117 intersecting with airflow from another hole 117.

c) The taper angle of the hole walls 117A, B−, B+, is varied on each side of the hole 117 relative to the draw direction 121.

d) Hole H1 has a taper angle β− on the left side, when viewed in transverse cross section, which is greater than the left side taper angles β− of holes H2 and H3.

e) Hole H1 has a taper angle β+ on the right side wall of 0°, such that the side wall 117A is parallel with the draw direction 121 at that cross-sectioned point. An angle any less than this may result in an undercut being formed that prevents the holes 117 being formed by a tool with a single draw angle. Preferably this taper angle should be no less than 1° for effective and durable tooling.

f) Holes H2 and H3 have a taper angle β+ on the right side wall 117A that is larger than the taper angle β+ of hole H1.

g) the combined left and right side wall taper angles (β−)+(β+) of each hole 117 forms a draft angle over which the airflow is dispersed, and determines the draft direction 127. This draft angle is between 2° and 20°.

The taper angles β of the vent hole side walls 117A also defines an angle δ between the vent hole side walls 117A and the inner surface 115B of the vent substrate 115A.

a) In this scenario where the vent holes 117 are located in a planar substrate 115A, and the draw direction 121 is perpendicular to the planar substrate 115A, the angle δ=90°−β.

b) An angle δ that is relatively small creates a sharp edge on at least part of the vent hole 117, which may undesirably increase noise when air flows past it.

c) It is desirable that the taper angles β+ and β− are always greater than 0° in order to provide some draft on the tool to aid in removal of the molded part from the tool.

Figure 11A:
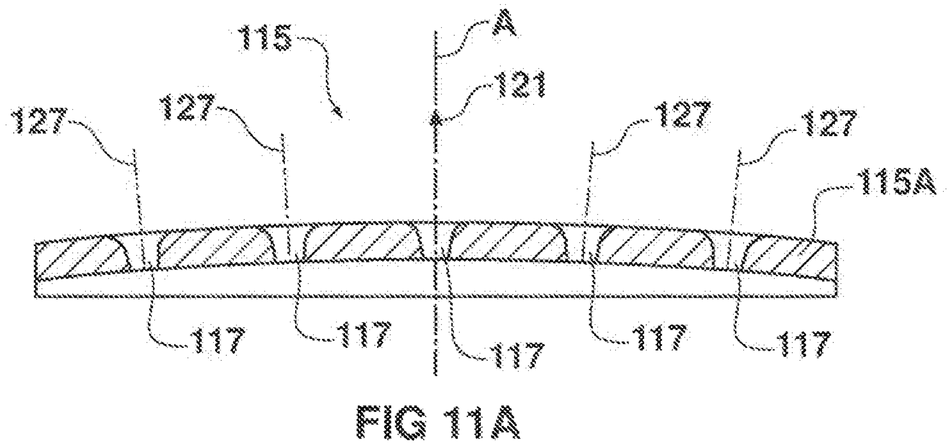
FIGS. 11*a* and 11*b* are sectional side views of another embodiment of a vent in accordance with the present invention, indicating the draft direction and draw direction.
Figure 11B:
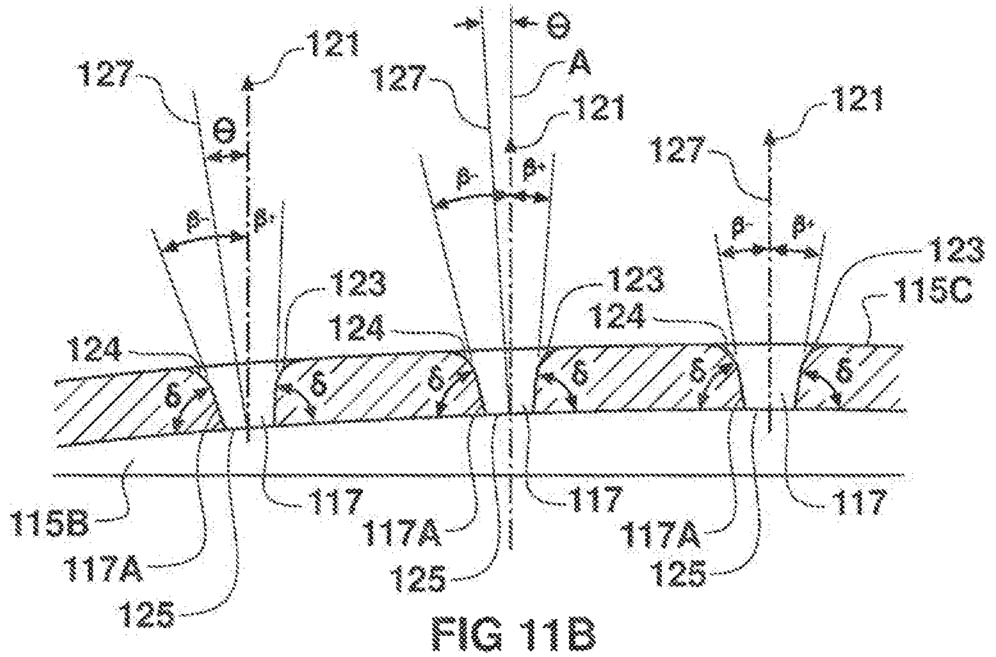
Figure 12:
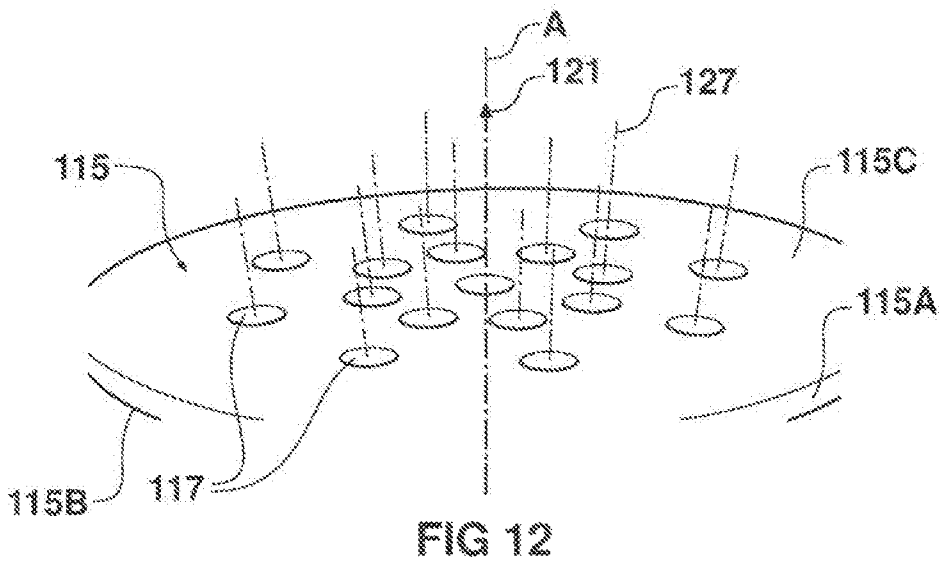
FIG. 12 is a perspective view of part of a further embodiment of a vent in accordance with the present invention, indicating the draft direction and draw direction.

With reference to FIGS. 11A and 11B, the vent holes 117 in the vent 115 are illustrated in an example vent substrate 115A which is substantially arcuate. The vent substrate 115A may be arcuate in two dimensions or in the three dimensions, as required. Part of a vent substrate 115A that is arcuate in three dimensions is shown in FIG. 12.

In this example, each vent hole 117 has tapered or inclined side walls 117A, in that the side walls 117A, in transverse cross section, are angled relative to the draw direction indicated by arrow 121. The exhaust gas outlet 123 has a larger diameter than the exhaust gas inlet 125. The exhaust gas outlet 123 is radiused 124. The exhaust gas outlet 123 and the exhaust gas inlet 125 each have a notional centre point, a vent hole axis 127 passing through the notional centre point of the outlet and inlet 123, 125. This vent hole axis 127 defines the draft direction of each vent hole 117. In this example, the draft direction 127 of the middle vent hole 117, labelled hole H3, is aligned with the draw direction 121, whilst the draft directions 127 of the outer vent holes 117, labelled hole H2 and hole H3 are inclined outwardly from the draw direction 121. Thus each vent hole 117 has a common, identical draw direction 121, but a different draft direction 127, with the angle of inclination between the draft direction 127 and the draw direction 121 increasing as the vent holes 117 are further from the middle vent hole 117, hole H3. Thus, the outermost vent hole 117, hole H1, disperses the exhausted gases at a greater angle relative to the draw direction 121 than the innermost vent holes 117, holes H2 and H3. The arcuate or curved vent substrate 115A may be configured to accentuate the angle of dispersion of the exhaust gases, that is, to increase the inclination of the draft direction 127 to the draw direction 121 of the outer vent holes 117, as compared to the planar substrate 115A of FIGS. 10A and 10B above.

The shape and configuration of vent holes 117 can be seen in more detail with reference to FIG. 11*b*, which is an enlarged view of FIG. 11*a*, above.

The draw direction 121 of the vent holes 117 is perpendicular to the inner surface 115B at a central or mid-point of the bias flow vent 115, that is at hole H3, when the vent 115 is viewed in transverse cross section. The draft direction 127 (θ) and the taper angles β− and β+ are substantially the same for that central hole H3.

The angle δ between the vent hole side walls 117A and the inner surface 115B is now defined by the taper angle in combination with the curvature of the inner surface 115B. In this scenario where the vent holes 117 are located in a curved substrate 115A the draw direction 121 is perpendicular to the substrate 115A only at the centre point of the bias flow vent 115 (the centre of hole H3 in this example). Therefore the angle δ is dependent on the angle of the inner surface 115B relative to the draw direction 121 radially outward from the centre of each individual hole 117.

The further a vent hole 117 is displaced outwardly from the centre of the bias flow vent 115 the greater the curvature of the substrate 115A relative to the draw plane/draw direction 121. The curvature of the substrate 115A combined with the taper of the hole side walls 117A increases the angle δ on the edges of the vent hole that are distal to the centre of the bias flow vent 115, compared to the same vent hole 117 in a planar substrate 115A. This helps to reduce the noise level generated by the bias flow vent 115. Reducing the angle δ can increase turbulence and increase noise.

The taper angle of each side wall 117A is asymmetric about the circumference of each hole 117, that is, the taper angle varies about the circumference.

Reference is also made to FIG. 12 which shows the vent substrate 115A being arcuate in three dimensions. Each of the vent holes 117 has a different draft direction 127, and the draft directions 127 of the vent holes 117 radiate outwards from the centre of the bias flow vent 115. The draft directions 117 are defined to fan outwardly of the notional centre axis A of the vent 115, such that the further a vent hole 117 is from the centre of the bias flow vent 115, the greater the angle of inclination between the draft direction 127 and the draw direction 121 will be.

For a vent substrate 115A that is arcuate in three dimensions, the draft direction 127 is determined in two dimensions i.e. in an x and a y dimension relative to the draw direction 121, and perpendicular to notional longitudinal axis A. The taper angle can also be different in the x and y directions.

Figure 13:
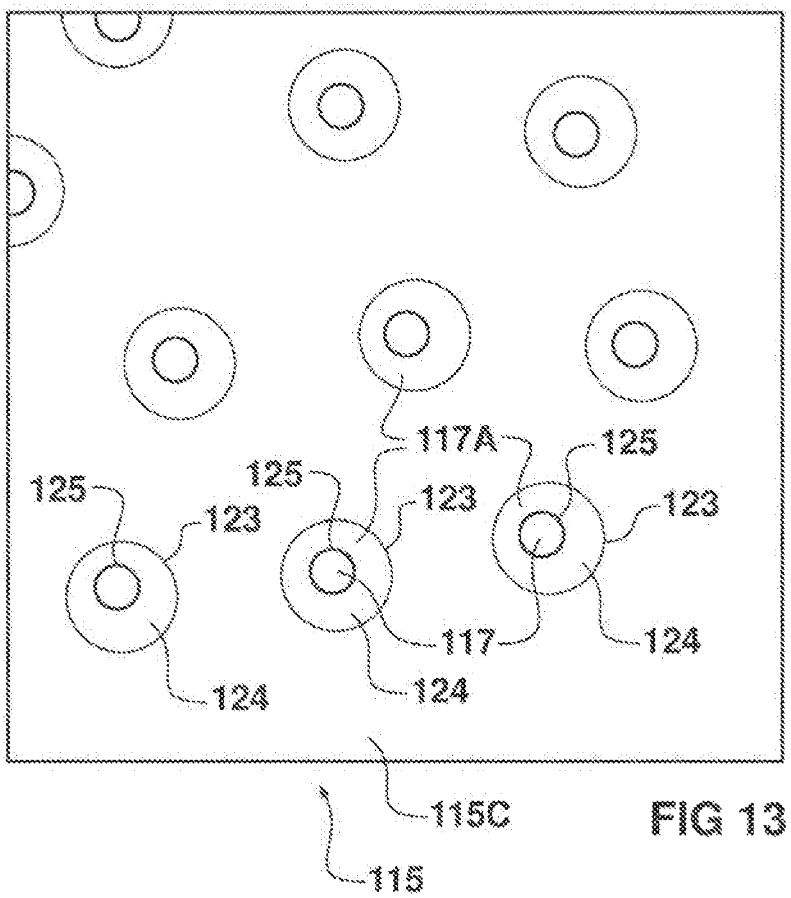
FIG. 13 is a plan view of the vent of FIG. 12.

With reference to FIG. 13, the different sizes of the exhaust gas outlet 123 and inlet 125 of each vent 117 can be seen, in the example where the exhaust gas outlet 123 is radiused 124. It can be seen that, when viewed from above, the outlet 123 and inlet 125 are not concentric, such that the notional centre of the outlet 123 at the outer surface 115C of the substrate 115A is offset from the notional centre of the inlet 125 at the inner surface 115B of the substrate 115A. FIG. 13 helps demonstrate the way in which the taper angles of the vent hole side walls 117A are different in each dimension. The maximum (outer) diameter of each vent hole 117 is offset from the minimum (inner) diameter of each vent hole 117 by a different amount in both the x and y directions, when the vent 115 is viewed from above.

Figure 14A:
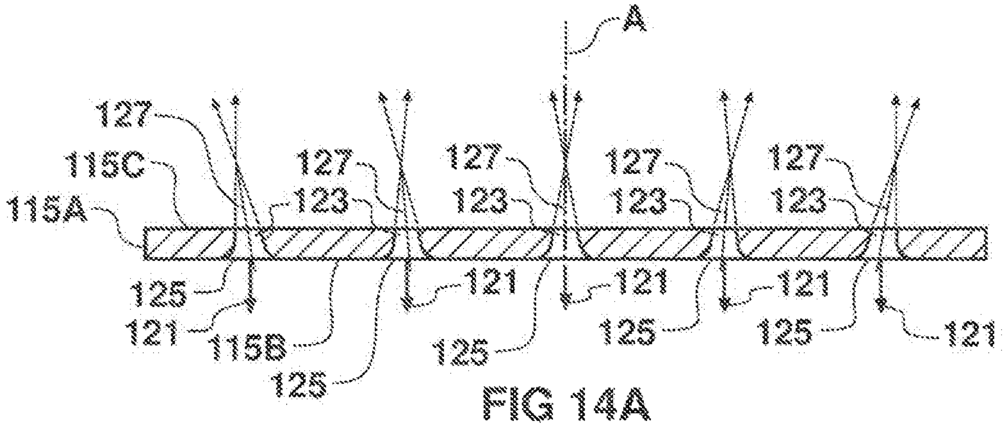
FIGS. 14*a* and 14*b* are sectional side views of a yet further embodiment of a vent in accordance with the present invention, indicating the draft direction and draw direction.
Figure 14B:
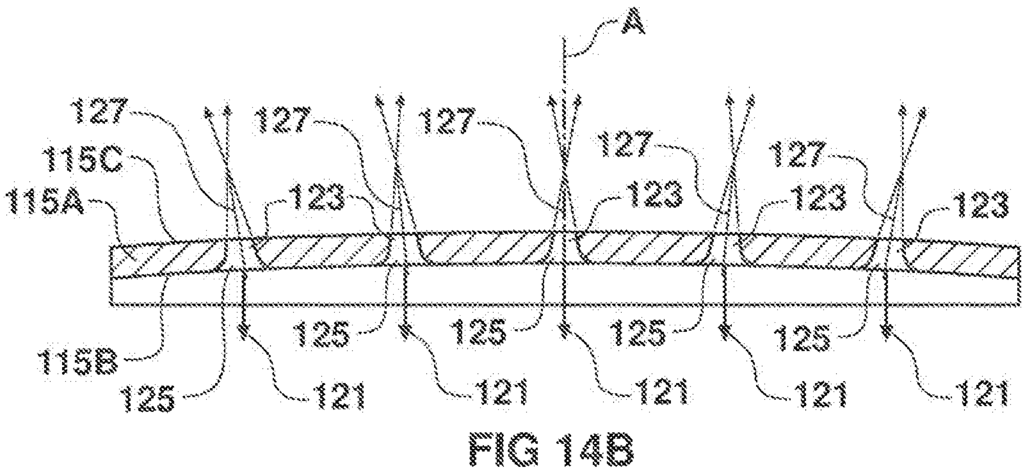

Referring to FIGS. 14A and 14B, further embodiments of a vent 115 in accordance with the present invention are provided, where the vent holes 117 are have a smaller diameter exhaust gas outlet 123 and a larger diameter exhaust gas inlet 125, the inlet 125 in these examples being radiused 124. In these examples, one of which is for a planar vent substrate 115A and the other for an arcuate vent substrate 115A, the vent holes 117 are formed from the inside of the vent 115, such that the draw direction 121 is downward in the figures, rather than upward, in the direction from the outer substrate surface 115B to the inside substrate surface 115B. The minimum diameter, that defines the flow rate through the vent 115, is on the outer surface 115C. This arrangement may reduce the amount of interference between air flow paths reducing air disturbance and noise. The draft directions 126 and draw direction 121 are illustrated in each Figure.

The above described vent 115 may comprise a separate vent component or module, for mounting on, or comprising part of, a respiratory therapy system, or may be integrally formed with part of a respiratory therapy system.

In one embodiment, the vent 115 may comprise part of a component being a patient interface. In the above described examples, the patient interface comprises a full face mask, but in other examples, the patient interface could any one of:

a) a nasal interface configured to seal around the nares or nose of the patient;

b) an oral mask configured to seal around the mouth of the patient; or c) a full face mask configured to seal around both the mouth and nose of the patient.

The vent 115 may be located at any suitable and/or desirable part of a respiratory therapy system, and in any suitable and/or desired component comprising part of such a system. It is envisaged that the vent 115 may there comprise part of, or be configured to be mounted on or connected to a component comprising any one of:

a) an elbow connector configured to connect a gas delivery conduit to a patient interface;

b) a gas delivery conduit;

c) a gas delivery conduit connector configured to connect a gas delivery conduit to another component.

The vent may comprise part of a respiratory therapy system which comprises any one or more of:

a) a breathing gas flow generator;

b) a breathing gas humidifier;

c) a gas delivery conduit, which may or may not be heated;

d) a patient interface.

Any suitable number of vent holes 117 may be provided as required, and the vent array may be any size, dependent upon the flow rate of gas to be vented, and the surface area available for venting.

The vent array may be arranged in two or more sub arrays, each sub array having the same or a different number of vent holes 117 as another. The arrangement, spacing, shape and/or configuration of vent holes 117 on one sub array may be the same or different as that of vent holes 117 on another sub array. For example, each sub array may comprise, relative to another sub array, vent holes having any one or more of:

a) a different draw direction;

b) a different draft direction;

c) a different exhaust gas outlet shape and/or diameter;

d) a different exhaust gas inlet shape and/or diameter;

e) vent holes side walls having differing taper angles;

f) different radiusing/chamfering of the exhaust gas outlet and/or the exhaust gas inlet;

g) different number of vents;

h) different spacing of vents;

i) different pattern of vents; and/or j) different length of each vent hole.

Unless the context clearly requires otherwise, throughout the description, the words "comprise", "comprising", and the like, are to be construed in an inclusive sense as opposed to an exclusive or exhaustive sense, that is to say, in the sense of "including, but not limited to".

Although this invention has been described by way of example and with reference to possible embodiments thereof, it is to be understood that modifications or improvements may be made thereto without departing from the scope of the invention. The invention may also be said broadly to consist in the parts, elements and features referred to or indicated in the specification of the application, individually or collectively, in any or all combinations of two or more of said parts, elements or features. Furthermore, where reference has been made to specific components or integers of the invention having known equivalents, then such equivalents are herein incorporated as if individually set forth.

Any discussion of the prior art throughout the specification should in no way be considered as an admission that such prior art is widely known or forms part of common general knowledge in the field.

The invention claimed is:

1. A respiratory therapy system comprising a vent, the vent comprising:

a substrate having an inner surface and an outer surface;

a longitudinal axis extending through the inner surface and the outer surface at a center of the vent; and a plurality of vent holes extending through the substrate, each of the plurality of vent holes having a vent hole circumference, each of the plurality of vent holes comprising:

an exhaust gas inlet at the inner surface of the substrate and an exhaust gas outlet at the outer surface of the substrate, the exhaust gas inlet and the exhaust gas outlet each having a notional center point, a vent hole draft direction axis passing through the notional center point of the exhaust gas inlet and the notional center point of the exhaust gas outlet, thereby defining a draft direction of each vent hole, a sidewall extending between the exhaust gas inlet and the exhaust gas outlet, an angle between the sidewall and the inner surface of the substrate is less than 90 degrees around the vent hole circumference, the angle between the sidewall and the inner surface of the substrate varying between the inner surface and the outer surface; and a draw direction axis passing through the exhaust gas outlet and the notional center point of the exhaust gas inlet, the draw direction axis forming an angle with the sidewall between 0 and 25 degrees, thereby defining a draw direction of each vent hole;

wherein the exhaust gas inlet has a smaller diameter than the exhaust gas outlet such that the sidewall is inclined;

wherein the vent hole draft direction axes of vent holes further from a center of the vent are inclined at a greater angle from the longitudinal axis relative to the vent hole draft direction axes of vent holes closer to the center of the vent, the vent hole draft direction axis of each vent hole being non-parallel to every other vent hole draft direction axis of the plurality of vent holes; and wherein the draw direction axes of the plurality of vent holes are parallel with each other.

2. The respiratory system of claim 1 wherein the plurality of vent holes comprises ten or more vent holes.

3. The respiratory system of claim 1 wherein the substrate comprises a substantially planar substrate portion, the plurality of vent holes being spaced apart on the substantially planar substrate portion.

4. The respiratory system of claim 1 wherein the substrate comprises an arcuate substrate portion, the plurality of vent holes being spaced apart on the arcuate substrate portion.

5. The respiratory system of claim 4 wherein the arcuate substrate portion is curved in two dimensions.

6. The respiratory system of claim 4 wherein the arcuate substrate portion is curved transversely across the vent, that is, when the vent is viewed in transverse cross section.

7. The respiratory system of claim 6 wherein the plurality of vent holes are spaced transversely across the vent, with each vent hole having a different draft direction, when viewed in transverse cross section.

8. The respiratory system of claim 6 wherein the plurality of vent holes are spaced longitudinally along the vent.

9. The respiratory system of claim 4 wherein the arcuate substrate portion is curved in three dimensions, both when the vent is viewed in transverse cross section and in longitudinal cross section.

10. The respiratory system of claim 1 wherein the draft direction of at least one vent hole is inclined relative to the longitudinal axis of the vent, when the at least one vent hole of the plurality of vent holes is viewed in transverse cross section.

11. The respiratory system of claim 1 wherein the draft direction of at least one vent hole is inclined relative to the longitudinal axis of the vent, when the at least one vent hole of the plurality of vent holes is viewed in longitudinal cross section.

12. The respiratory system of claim 11 wherein the angle of inclination of the draft direction of the at least one vent hole relative to the longitudinal axis of the vent when the at least one vent hole of the plurality of vent holes is viewed in transverse cross section is different from the angle of inclination of the draft direction relative to the longitudinal axis of the vent when the at least one vent hole of the plurality of vent holes is viewed in the longitudinal cross section.

13. The respiratory system of claim 1, wherein for each of the plurality of vent holes, the exhaust gas inlet is entirely radially inward of the exhaust gas outlet.

14. The respiratory system of claim 1, wherein the angle between the sidewall and the inner surface of the substrate for each vent hole is non-constant around the vent hole circumference.

15. A mask comprising:

a mask shell; and the respiratory therapy system of claim 1, wherein the vent is integrally formed with the mask shell, the vent configured to exhaust gases from the mask shell.

* * * * *